US010591198B2

(12) United States Patent
Abeygunawardana et al.

(10) Patent No.: US 10,591,198 B2
(45) Date of Patent: Mar. 17, 2020

(54) REFRIGERATOR APPLIANCE AND METHODS OF OPERATION

(71) Applicant: Haier US Appliance Solutions, Inc., Wilmington, DE (US)

(72) Inventors: Danister Abeygunawardana, Louisville, KY (US); Bagawathkumar Chellappan, Louisville, KY (US); John Keith Besore, Prospect, KY (US); Pat Napier, Crestwood, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 191 days.

(21) Appl. No.: 15/622,212

(22) Filed: Jun. 14, 2017

(65) Prior Publication Data
US 2018/0363971 A1    Dec. 20, 2018

(51) Int. Cl.
*F25D 17/04* (2006.01)
*F25D 17/06* (2006.01)
*A61L 9/015* (2006.01)
*A61L 2/20* (2006.01)

(52) U.S. Cl.
CPC ......... *F25D 17/042* (2013.01); *F25D 17/062* (2013.01); *A23V 2250/128* (2013.01); *A61L 2/202* (2013.01); *A61L 9/015* (2013.01); *F25D 2317/0416* (2013.01)

(58) Field of Classification Search
CPC .. F25D 17/042; F25D 17/062; F25D 2317/04; F25D 2317/041; F25D 2317/0415; F25D 2317/0416; F25D 2317/0417; F25D 2317/043; F24F 2110/74;
(Continued)

(56) References Cited

U.S. PATENT DOCUMENTS 2,851,366 A  * 9/1958  Schaefer .............. A23L 3/3418
                                                    426/235
5,034,032 A  * 7/1991  Yikai .................... B01D 46/00
                                                    96/55
(Continued)

FOREIGN PATENT DOCUMENTS

CN          2663887 Y     12/2004
JP          5248275 B2     7/2013
KR        100789814 B1    12/2007

*Primary Examiner* — Cassey D Bauer
*Assistant Examiner* — Miguel A Diaz
(74) *Attorney, Agent, or Firm* — Dority & Manning, P.A.

(57) ABSTRACT

A refrigerator appliance and methods of operation are provided herein. The refrigerator appliance may include a cabinet, a storage bin, a lid, an ozone passage, an air conduit, an air handler, and an ozone filter. The storage bin may include a plurality of walls defining a storage volume. The lid may be positioned on the storage bin to selectively cover the storage volume in a closed position. The ozone passage may be defined through at least one of the plurality of walls in fluid communication with the storage volume. The air conduit may be disposed in selective fluid communication with the ozone passage. The air handler may be disposed in fluid communication with the air conduit to direct ozone through the ozone passage. The ozone filter may be disposed in fluid communication with the air conduit to filter ozone passing from the storage volume through the air conduit.

17 Claims, 10 Drawing Sheets

(58) Field of Classification Search
CPC ....... F24F 2003/1671; A23V 2250/128; A61L 2/202; A61L 9/015; A61M 2202/0216
See application file for complete search history.

(56) References Cited

U.S. PATENT DOCUMENTS

| | | | | |
|---|---|---|---|---|
| 5,230,220 | A * | 7/1993 | Kang | A61L 9/015 422/121 |
| 5,501,084 | A * | 3/1996 | Chang | F25D 17/042 62/264 |
| 6,167,711 | B1 * | 1/2001 | Slattery | A61L 2/202 62/344 |
| 6,481,219 | B2 * | 11/2002 | Palermo | A61L 2/202 62/51.1 |
| 6,865,896 | B2 * | 3/2005 | Kaji | A61L 9/22 250/382 |
| 6,923,015 | B2 * | 8/2005 | Ueno | A61L 9/16 422/121 |
| 7,056,476 | B2 * | 6/2006 | Okada | A61L 9/015 422/121 |
| 9,093,258 | B2 * | 7/2015 | Stibich | A61L 2/10 |
| 9,340,288 | B2 * | 5/2016 | Vandyke | B62B 3/005 |
| 9,399,834 | B1 * | 7/2016 | Drake | D06M 11/34 |
| 9,482,459 | B2 * | 11/2016 | Park | F25D 11/00 |
| 2002/0037240 | A1 * | 3/2002 | Okada | A61L 9/015 422/124 |
| 2006/0053828 | A1 * | 3/2006 | Shallman | F25D 3/14 62/457.9 |
| 2010/0243767 | A1 * | 9/2010 | Mori | A23L 3/375 239/691 |
| 2013/0059047 | A1 * | 3/2013 | Arrigo | A23B 7/148 426/320 |
| 2013/0340465 | A1 * | 12/2013 | Park | F25D 11/00 62/376 |
| 2017/0350635 | A1 * | 12/2017 | Thirumurugavel | F25D 3/14 |
| 2018/0099062 | A1 * | 4/2018 | Campalans | F25B 21/04 |
| 2019/0063763 | A1 * | 2/2019 | Kleinberger | A61L 2/022 |

* cited by examiner

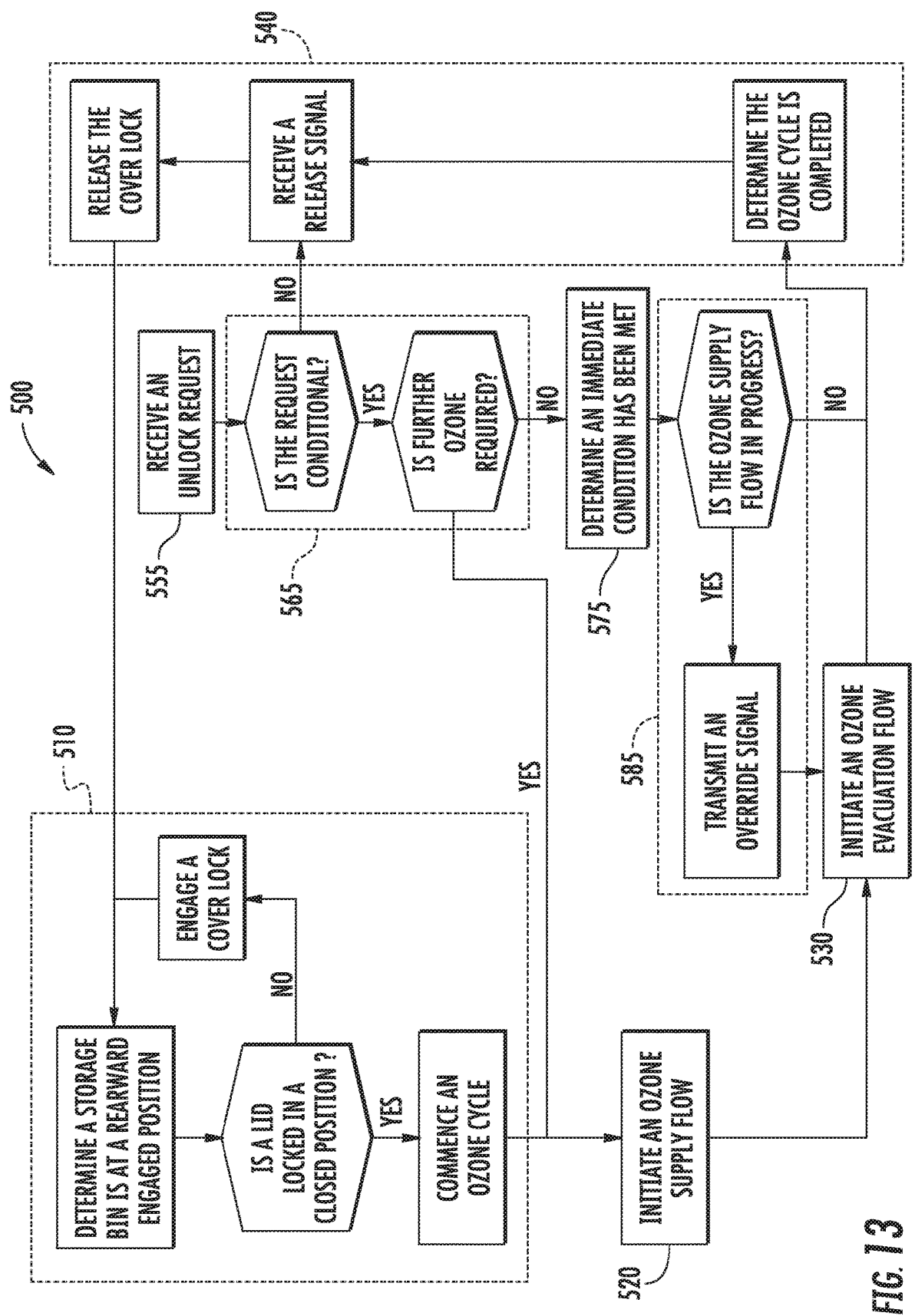

REFRIGERATOR APPLIANCE AND METHODS OF OPERATION

FIELD OF THE INVENTION

The present subject matter relates generally to refrigerator appliance, and more particularly to refrigerator appliances having one or more features for ozone cleaning.

BACKGROUND OF THE INVENTION

Domestic appliances, such as refrigerator appliances, generally include a cabinet that defines an internal chamber. In the case of refrigerator appliances, a chilled chamber may be defined for receipt of food articles for storage. Refrigerator appliances can also include various storage components mounted within the chilled chamber and designed to facilitate storage of food items therein. Such storage components can include racks, bins, shelves, or drawers that receive food items and assist with organizing and arranging of such food items within the chilled chamber.

Although the relatively low temperatures within the chilled chamber of a refrigerator appliance serve to preserve food within the appliance, some refrigerator appliances include one or more features to assist with food preservation. For instance, certain existing appliances include an ozone generator for producing gaseous ozone (i.e., $O_3$) within the chilled chamber. The produced gaseous ozone may effectively eliminate or reduce bacteria and fungi within the chilled chamber, thereby preserving food items and reducing undesired odors. This can be especially useful in the context of storing fruits and vegetables.

Existing systems present several disadvantages and limitations. While gaseous ozone can be useful for preserving certain food items, it can lead to certain health risks if inhaled in large amounts. For instance, large concentrations ozone [e.g., ozone in concentrations above 50 parts per billion (ppb)] may cause respiratory irritation. However, such concentrations may be more effective at preserving food items. Ozone generated within a refrigerator may eventually break down as oxygen (i.e., $O_2$), but the process can be relatively slow. A user rapidly or repeatedly opening a door to access the chilled chamber may risk exposure to unhealthful concentrations or amounts of ozone. Although some systems attempt to limit the location of ozone within a chilled chamber, such systems have not provided adequate performance or safety.

In turn, further improvements are necessary to refrigerator appliances to utilize ozone within a chilled chamber. In particular, a refrigerator appliance having one or more features for generating ozone within the appliance while preventing undesirable exposure for users would be useful.

BRIEF DESCRIPTION OF THE INVENTION

Aspects and advantages of the invention will be set forth in part in the following description, or may be obvious from the description, or may be learned through practice of the invention.

In one aspect of the present disclosure a refrigerator appliance is provided. The refrigerator appliance may include a cabinet defining a chilled chamber, a storage bin, a lid, an ozone passage, an air conduit, an air handler, and an ozone filter. The storage bin may be positioned within the chilled chamber. The storage bin may include a plurality of walls defining a storage volume. The lid may be positioned on the storage bin to selectively cover the storage volume in a closed position. The ozone passage may be defined through at least one of the plurality of walls in fluid communication with the storage volume. The air conduit may be disposed in selective fluid communication with the ozone passage. The air handler may be disposed in fluid communication with the air conduit to direct ozone through the ozone passage. The ozone filter may be disposed in fluid communication with the air conduit to filter ozone passing from the storage volume through the air conduit.

In another aspect of the present disclosure, a method of operating a refrigerator appliance is provided. The method may include one or more steps. The steps may include receiving a closed lid signal from a position sensor in operable communication with the lid; initiating a supply flow of ozone in a first flow direction from an air conduit to the storage volume in response to receiving the closed lid signal; receiving an ozone evacuation command; and/or initiating an evacuation flow of ozone in a second flow direction from the storage volume to an air conduit in response to receiving the ozone evacuation command.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

FIG. 13 provides a flow chart illustrating a method of operating a refrigerator appliance in accordance with example embodiments of the present disclosure.

DETAILED DESCRIPTION

Figure 1:
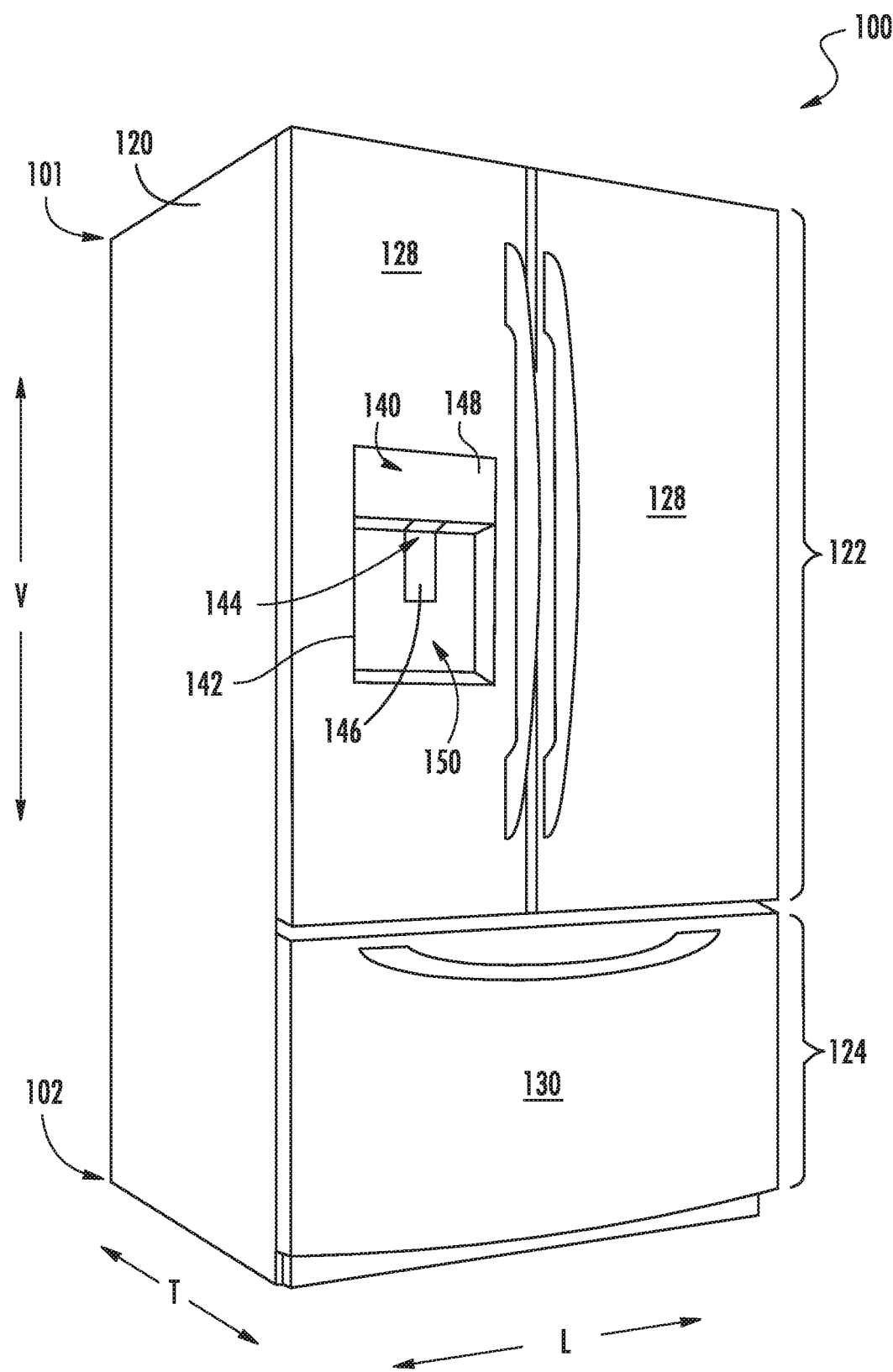
FIG. 1 provides a perspective view of a refrigerator appliance according to example embodiments of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure provides a refrigerator appliance that has a storage bin and lid within a chilled chamber. An air handler may be provided to direct ozone to a storage volume defined by the storage bin. The lid may prevent ozone from passing to the rest of the chilled chamber. Additional features and methods may be provided to further limit a user's exposure to ozone, as will be described in detail below.

Figure 2:
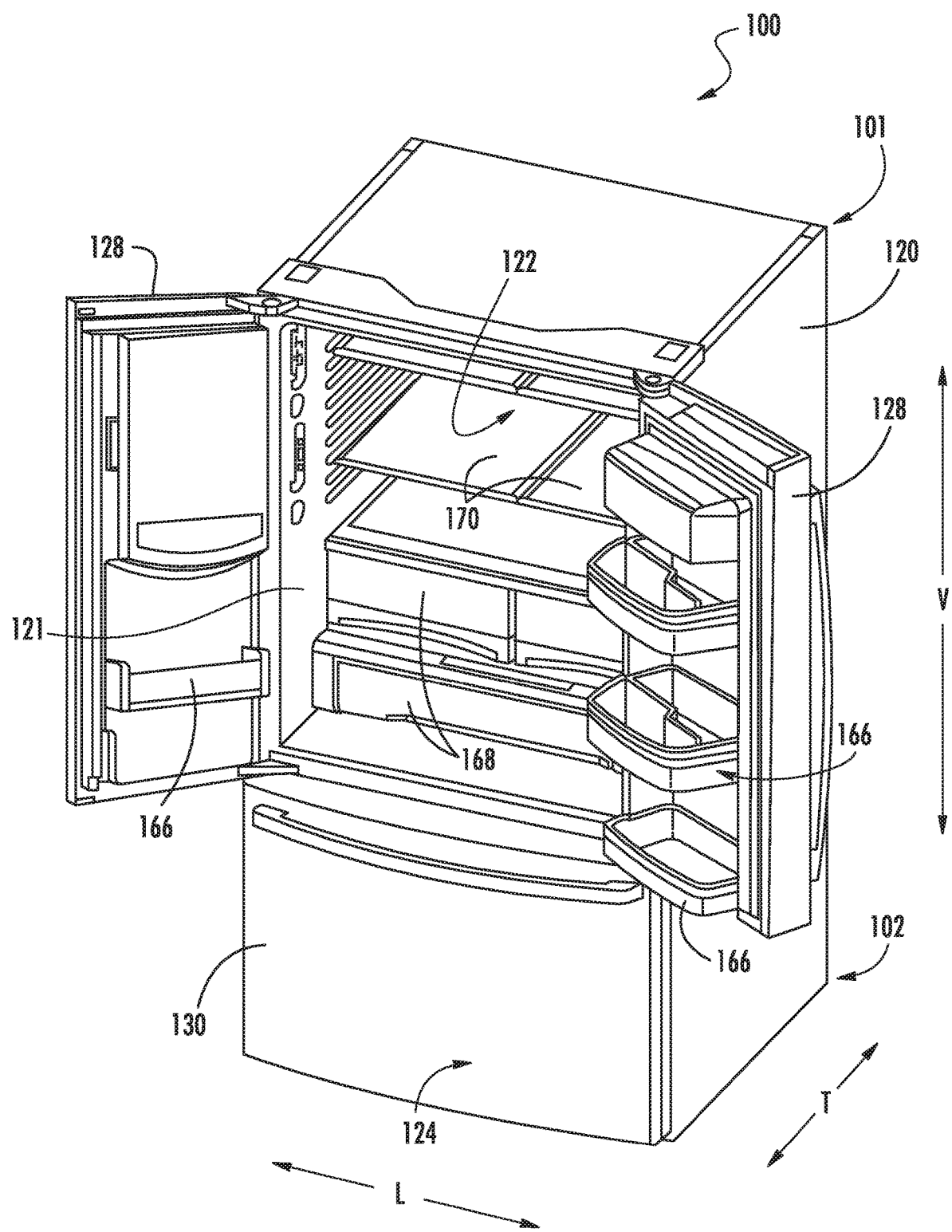
FIG. 2 provides a perspective view of the example refrigerator appliance of FIG. 1, wherein refrigerator doors of the refrigerator appliance are in an open position to reveal a fresh food chamber of the refrigerator appliance.

Turning now to the figures, FIGS. 1 and 2, FIG. 1 provides a perspective view of a refrigerator appliance 100 according to an example embodiment of the present disclosure. FIG. 2 provides a perspective view of refrigerator appliance 100 having multiple refrigerator doors 128 in the open position. As shown, refrigerator appliance 100 includes a cabinet or cabinet 120 that extends between a top 101 and a bottom 102 along a vertical direction V. Cabinet 120 also extends along a lateral direction L and a transverse direction T, each of the vertical direction V, lateral direction L, and transverse direction T being mutually perpendicular to one another. In turn, vertical direction V, lateral direction L, and transverse direction T defines an orthogonal direction system.

Cabinet 120 includes a liner 121 that defines chilled chambers for receipt of food items for storage. In particular, liner 121 defines a fresh food chamber 122 positioned at or adjacent top 101 of cabinet 120 and a freezer chamber 124 arranged at or adjacent bottom 102 of cabinet 120. As such, refrigerator appliance 100 is generally referred to as a bottom mount refrigerator. It is recognized, however, that the benefits of the present disclosure apply to other types and styles of appliances such as, e.g., a top mount refrigerator appliance, a side-by-side style refrigerator appliance, or a range appliance. Consequently, the description set forth herein is for illustrative purposes only and is not intended to be limiting in any aspect to any particular refrigerator chamber configuration.

Refrigerator doors 128 are rotatably hinged to an edge of cabinet 120 for selectively accessing fresh food chamber 122. In addition, a freezer door 130 is arranged below refrigerator doors 128 for selectively accessing freezer chamber 124. Freezer door 130 is attached to a freezer drawer (not shown) slidably mounted within freezer chamber 124. Refrigerator doors 128 and freezer door 130 are shown in the closed configuration in FIG. 1.

In some embodiments, refrigerator appliance 100 also includes a dispensing assembly 140 for dispensing liquid water and/or ice. Dispensing assembly 140 includes a dispenser 142 positioned on or mounted to an exterior portion of refrigerator appliance 100, e.g., on one of refrigerator doors 128. Dispenser 142 includes a discharging outlet 144 for accessing ice and liquid water. An actuating mechanism 146, shown as a paddle, is mounted below discharging outlet 144 for operating dispenser 142. In alternative exemplary embodiments, any suitable actuating mechanism may be used to operate dispenser 142. For example, dispenser 142 can include a sensor (such as an ultrasonic sensor) or a button rather than the paddle. A user interface panel 148 is provided for controlling the mode of operation. For example, user interface panel 148 includes a plurality of user inputs (not labeled), such as a water dispensing button and an ice-dispensing button (e.g., for selecting a desired mode of operation such as crushed or non-crushed ice).

Discharging outlet 144 and actuating mechanism 146 are an external part of dispenser 142 and are mounted in a dispenser recess 150. Dispenser recess 150 is positioned at a predetermined elevation convenient for a user to access ice or water and enabling the user to access ice without the need to bend-over and without the need to open refrigerator doors 128.

According to the illustrated embodiment, various storage components are mounted within fresh food chamber 122 to facilitate storage of food items therein as will be understood by those skilled in the art. In particular, the storage components include storage bins 166, drawers 168, and shelves 170 that are mounted within fresh food chamber 122. Storage bins 166, drawers 168, and shelves 170 are configured for receipt of food items (e.g., beverages and/or solid food items) and may assist with organizing such food items. As an example, drawers 168 can receive fresh food items (e.g., vegetables, fruits, and/or cheeses) and increase the useful life of such fresh food items.

Operation of the refrigerator appliance 100 can be generally controlled or regulated by a controller 190. As will be described in greater detail below, controller 190 may include multiple modes of operation or sequences that control or regulate various portions of refrigerator appliance 100 according to one or more discrete criteria.

In some embodiments, controller 190 is operably coupled to user interface panel 148 and/or various other components, as will be described below. User interface panel 148 provides selections for user manipulation of the operation of refrigerator appliance 100. As an example, user interface panel 148 may provide for selections between whole or crushed ice, chilled water, and/or specific modes of operation. In response to one or more input signals (e.g., from user manipulation of user interface panel 148 and/or one or more sensor signals), controller 190 may operate various components of the refrigerator appliance 100.

Controller 190 may include a memory and one or more microprocessors, CPUs or the like, such as general or special purpose microprocessors operable to execute programming instructions or micro-control code associated with operation of refrigerator appliance 100. The memory may represent random access memory such as DRAM, or read only memory such as ROM or FLASH. In some embodiments, the processor executes non-transitory programming instructions stored in memory. For certain embodiments, the instructions include a software package configured to operate appliance 100 and, e.g., execute an operation routine including the example methods 400 and 500 described below with reference to FIGS. 12 and 13. The memory may be a separate component from the processor or may be included onboard within the processor. Alternatively, controller 190 may be constructed without using a microprocessor, e.g., using a combination of discrete analog and/or digital logic circuitry (such as switches, amplifiers, integrators, comparators, flip-flops, AND gates, and the like) to perform control functionality instead of relying upon software.

Controller 190, or portions thereof, may be positioned in a variety of locations throughout refrigerator appliance 100. In example embodiments, controller 190 is located within the user interface panel 148. In other embodiments, the controller 190 may be positioned at any suitable location within refrigerator appliance 100, such as for example within a fresh food chamber, a freezer door, etc. In additional or alternative embodiments, controller 190 is formed from multiple components mounted at discrete locations within or on refrigerator appliance 100. Input/output ("I/O") signals may be routed between controller 190 and various operational components of refrigerator appliance 100. For example, user interface panel 148 may be operably coupled (e.g., directly or indirectly electrically coupled) to controller 190 via one or more signal lines or shared communication busses.

Figure 3:
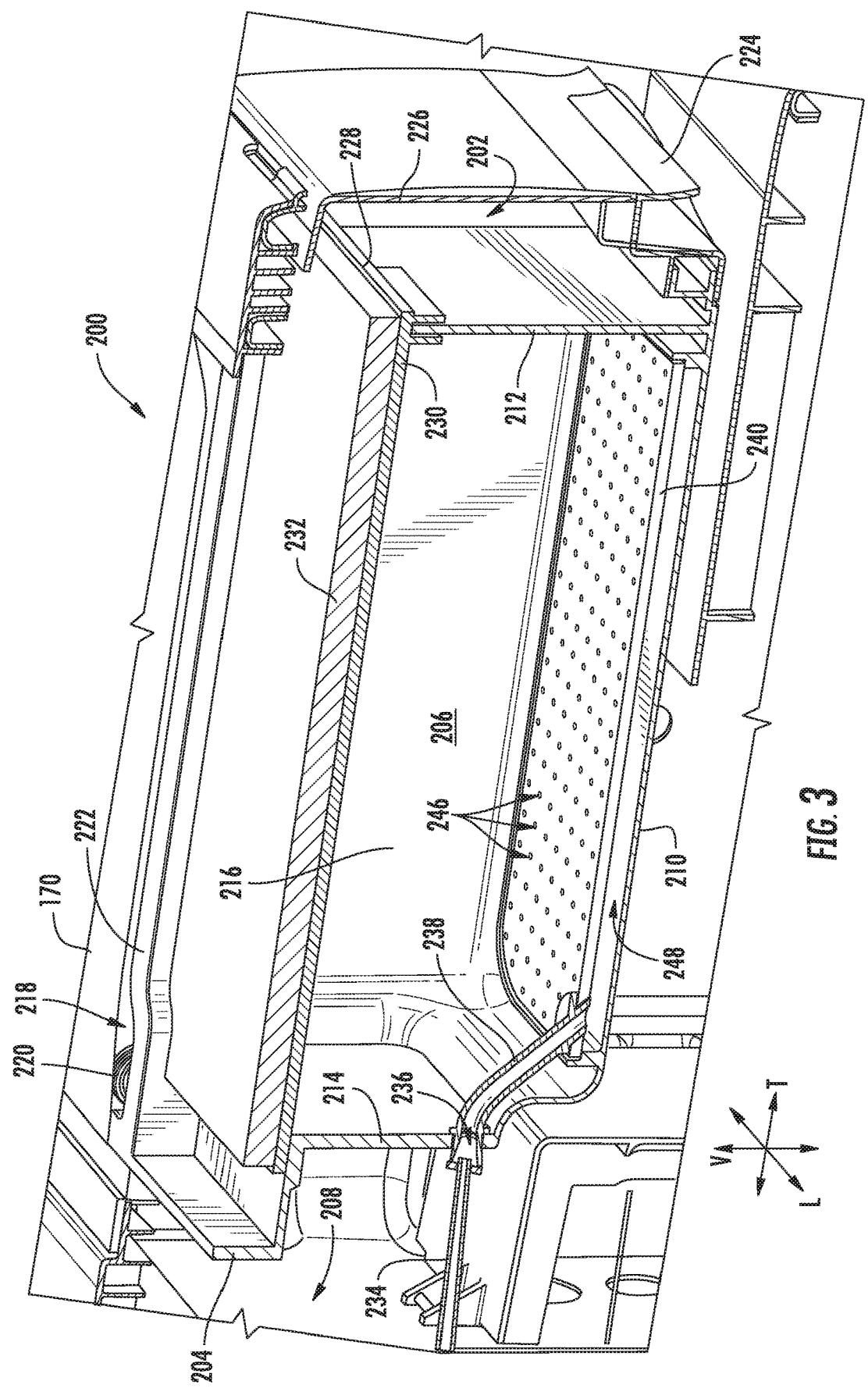
FIG. 3 provides a cross-sectional perspective view of a storage assembly of a refrigerator appliance according to example embodiments of the present disclosure.
Figure 4:
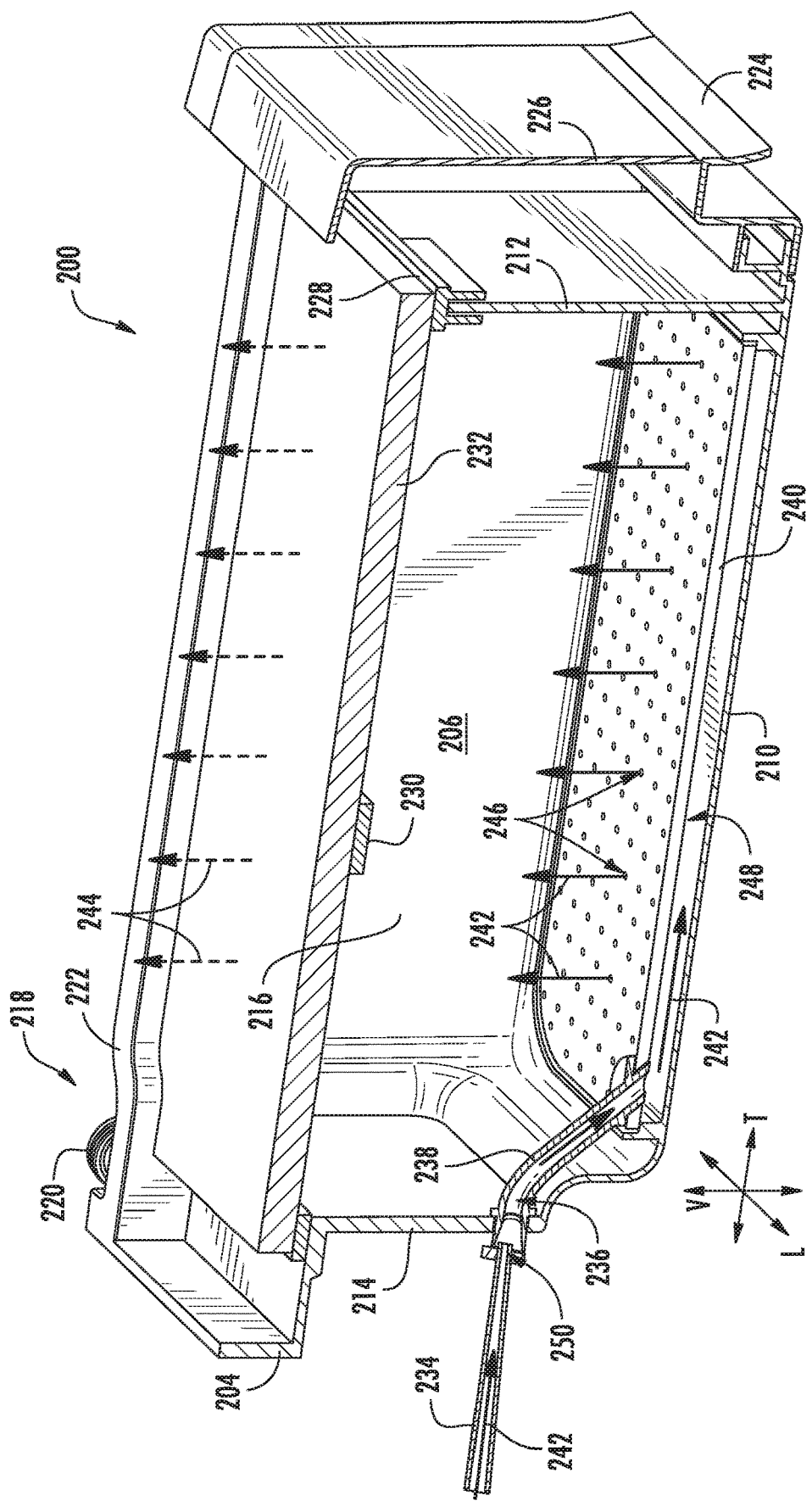
FIG. 4 provides a cross-sectional perspective view of the example storage assembly of FIG. 3 in an engaged position.
Figure 5:
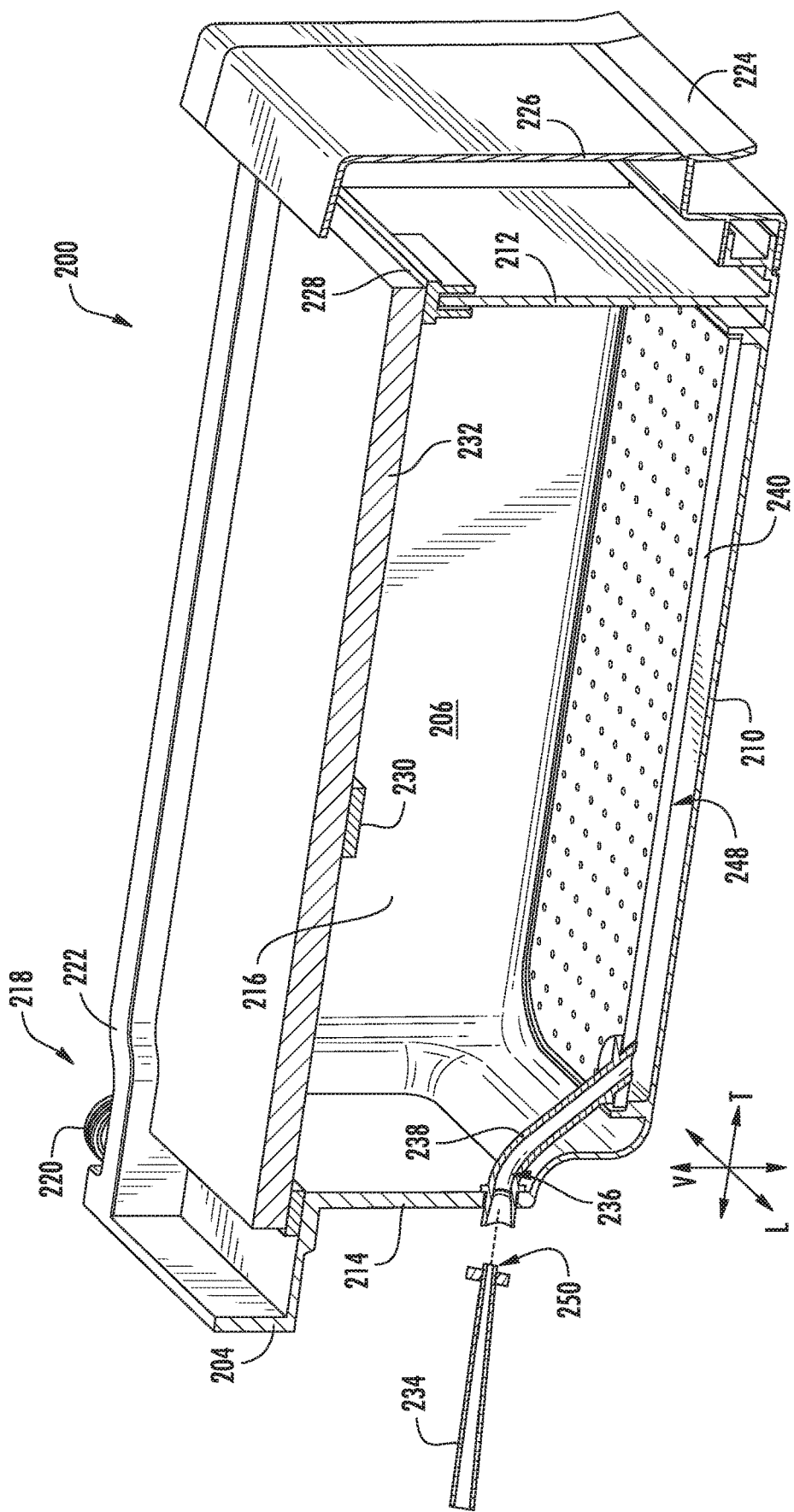
FIG. 5 provides a cross-sectional perspective view of the example storage assembly of FIG. 3 in an unengaged position.

Turning now to FIGS. 3 through 5, various perspective cross-sectional views of an example storage assembly 200 are shown. As illustrated in FIG. 3, storage assembly can be mounted within fresh food chamber 122. Storage assembly 200 is mounted to a portion of liner 121, e.g., at one or more sidewalls of liner 121. It is understood that storage assembly 200 may include, or be provided as, one or more of drawers 168 (FIG. 2). For example, storage assembly 200 may be mounted below a shelf 170 along the vertical direction V such that the bottom portion of the shelf 170 defines an upper limit of a cavity 202 into which at least a portion of storage assembly 200 may be removably and/or movably mounted.

As shown, storage assembly 200 may be positioned on or within a chilled chamber (e.g., fresh food chamber 122—FIG. 2) includes a storage bin 204 that has a plurality of walls defining a storage volume 206. For instance, storage bin 204 may include a base wall 210, as well as front wall 212, rear wall 214, and pair of sidewalls 216 extending from the base wall 210 (e.g., in the vertical direction V). The walls 210, 212, 214, 216 may be provided as an integral, unitary assembly or, alternatively, as a plurality of connected members. It is understood that some (e.g., all) of the walls 210, 212, 214, 216 may be substantially solid, non-permeable members such that air or ozone may not pass therethrough, except as otherwise indicated. When assembled, rear wall 214 may face a rear portion 208 of the fresh food chamber 122 (e.g., in the transverse direction T opposite the storage volume 206) while front wall 212 may face the opening selectively covered by door(s) 128 (FIG. 1) (e.g., in the transverse direction T opposite the storage volume 206).

As illustrated, storage bin 204 may be movably (e.g., slidably) mounted within the chilled chamber. In some such embodiments, a sliding assembly 218 is attached to storage bin 204. For instance, one or more bearings 220 may be rotatably fixed to a frame 222 of storage bin 204 within the cavity 202. Optionally, least one bearing may be attached to storage bin 204 laterally outward from each sidewall 216. However, alternative embodiments may include any suitably sliding member (e.g., below shelf 170). A front handle 224 may be further attached to storage bin 204. In some embodiments, handle 224 is positioned forward from front wall 212 along the transverse direction T. Additionally, some embodiments of handle 224 will include a forward panel 226 extending in the vertical direction V to or toward shelf 170 to further enclose cavity 202.

When assembled, storage bin 204, including sliding assembly 218, may selectively move between an engaged position (FIGS. 3 and 4) and an unengaged position (FIG. 5). In specific embodiments, storage bin 204 may slide along the transverse direction T. The engaged position may generally provide storage bin 204 rearward (e.g., proximal to the rear portion 208 of fresh food chamber 122—FIG. 2) while the unengaged position provides storage bin 204 forward (e.g., distal to the rear portion 208 of the fresh food chamber 122). In some such embodiments, the unengaged position extends storage bin 204 through a portion of the opening selectively covered by doors 128 (FIG. 1) and/or in front of at least a portion of shelf 170. Thus, cavity 202 and/or storage volume 206 may be accessible to a user in the unengaged position such that items may be added to and/or removed therefrom.

A lid 228 is positioned (e.g., selectively positioned) on storage bin 204. For instance, lid 228 may be positioned over storage volume 206 in the vertical direction V. When assembled, lid 228 may move (e.g., rotate) between an open position and a closed position. As illustrated in FIGS. 3 through 5, lid 228 in the closed position may extend across storage volume 206, engaging one or all of walls 210, 212, 214, 216 to cover the storage volume 206. In the closed position, lid 228 may selectively seal storage volume 206. Specifically, lid 228 may prevent a user from accessing storage volume 206. In other words, a user will be unable to insert food items into storage volume 206 or remove food items from storage volume 206. Additionally or alternatively, certain gases (e.g., gaseous ozone) may be prevented from passing to/from storage volume 206 through lid 228. Optionally, lid 228 may include a lid body 230 formed, for example, from a solid, non-permeable material. Lid may further include a lid filter 232, such as an ozone filter, held or positioned on lid body 230. In some embodiments, lid filter 232 may be an ozone filter formed from a semi-permeable material (e.g., activated carbon or charcoal) to break down gaseous ozone as it passes therethrough. Specifically, lid filter 232 may include one or more catalysts for facilitating or accelerating gaseous ozone decomposition. In the open position (not pictured) lid 228 may be lifted (e.g., rotated about a pivot access parallel to the lateral direction L) from the closed position and/or walls 210, 212, 214, 216, thereby permitting a user to readily access storage volume 206 (e.g., to add or remove food items within storage volume 206).

In some embodiments, an air conduit 234 is provided to selectively exchange one or more gases with storage volume 206. An ozone passage 236 may be defined through at least one of walls 210, 212, 214, 216 (e.g., rear wall 214) to permit such gases to and/or from storage volume 206. In other words, ozone passage 236 permits fluid communication between storage volume 206 and an area outside of storage bin 204. As shown, a secondary conduit 238 may further define a portion of ozone passage 236 (e.g., within a portion of storage volume 206). Specifically, secondary conduit 238 may extend from a wall (e.g., rear wall 214) of storage bin 204 to a distributor plate 240 mounted within storage volume 206. Distributor plate 240 may be positioned above base wall 210. Moreover, distributor plate 240 may be disposed in fluid communication between the ozone passage 236 and the storage volume 206. A plurality of apertures 246 are defined through distributor plate 240 (e.g., along the vertical direction V). In some such embodiments, ozone passage 236 directs gas from rear wall 214 to a flow cavity 248 defined between distributor plate 240 and base wall 210 (e.g., relative to the vertical direction V). Thus, gas may pass between air conduit 234 and distributor plate 240 through flow cavity 248.

When assembled, air conduit 234 may selectively engage ozone passage 236 in fluid communication therewith. For instance, air conduit 234 may be fixed at a position rearward of storage bin 204 along the transverse direction T (e.g., within cavity 202). In some such embodiments, air conduit 234 defines a port 250 behind storage bin 204 at the rear portion 208 of the fresh food chamber 122 (FIG. 2). Ozone passage 236 may be defined through the rear wall 214 to selectively engage the port 250. For instance, when storage bin 204 is moved to the engaged position, air conduit 234 may engage storage bin 204 in fluid communication with ozone passage 236 and storage volume 206. By contrast, when storage bin 204 is moved away the engaged position (e.g., to the unengaged position), air conduit 234 may be removed from storage bin 204 such that air conduit 234 does not contact, for example, rear wall 214. Additionally, storage bin 204 may be separated from air conduit 234 such that no direct fluid communication is provided between air conduit 234 and ozone passage 236 or storage volume 206. In some such embodiments, air conduit 234 is formed as a Morse taper to be sealingly received by ozone passage 236 in the engaged position. Additionally or alternatively, a fluid gasket or O-ring may be provided between air conduit 234 and ozone passage 236, thus ensuring a hermetic seal between air conduit 234 and storage bin 204 (e.g., at rear wall 214) in the engaged position.

During certain operations, ozone may be selectively provided to storage volume 206. For instance, as illustrated in FIG. 4, gaseous ozone (represented generally by arrows 242) may be directed from air conduit 234 through ozone passage 236 in the engaged position. From ozone passage 236, ozone 242 may be directed below distributor plate 240 before passing through one or more apertures 246. From apertures 246, gaseous ozone 242 may disperse within storage volume 206. In embodiments having a lid filter 232, ozone 242 may pass to lid filter 232, wherein gaseous ozone 242 is broken down into gaseous oxygen (represented generally by arrows 244).

Figure 6:
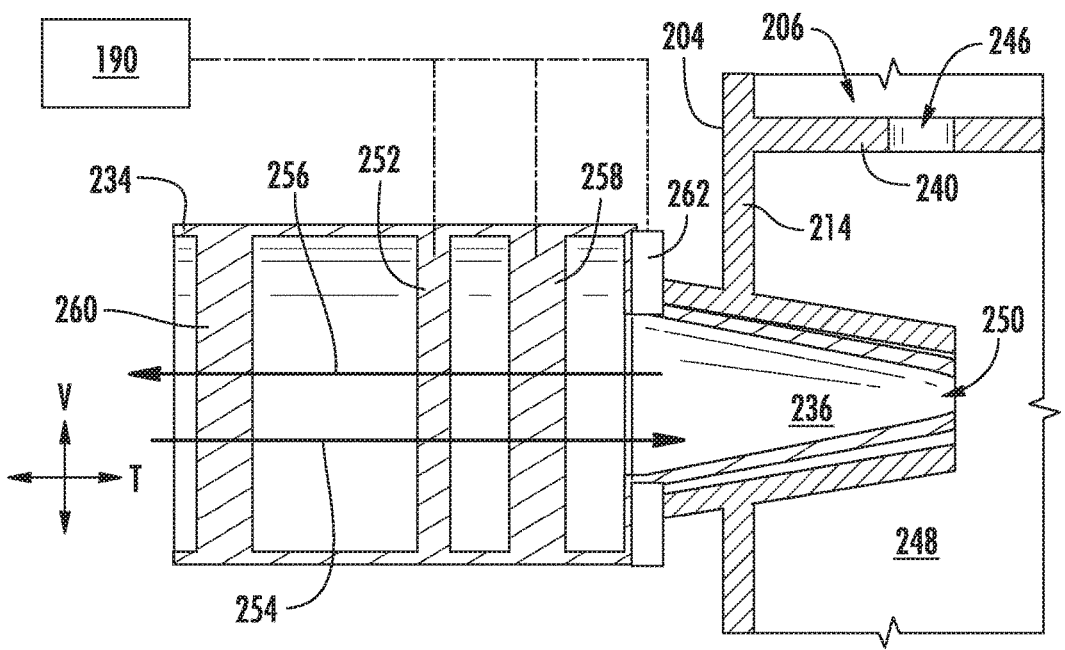
FIG. 6 provides a cross-sectional schematic view of a portion of an example storage assembly in an engaged position.
Figure 7:
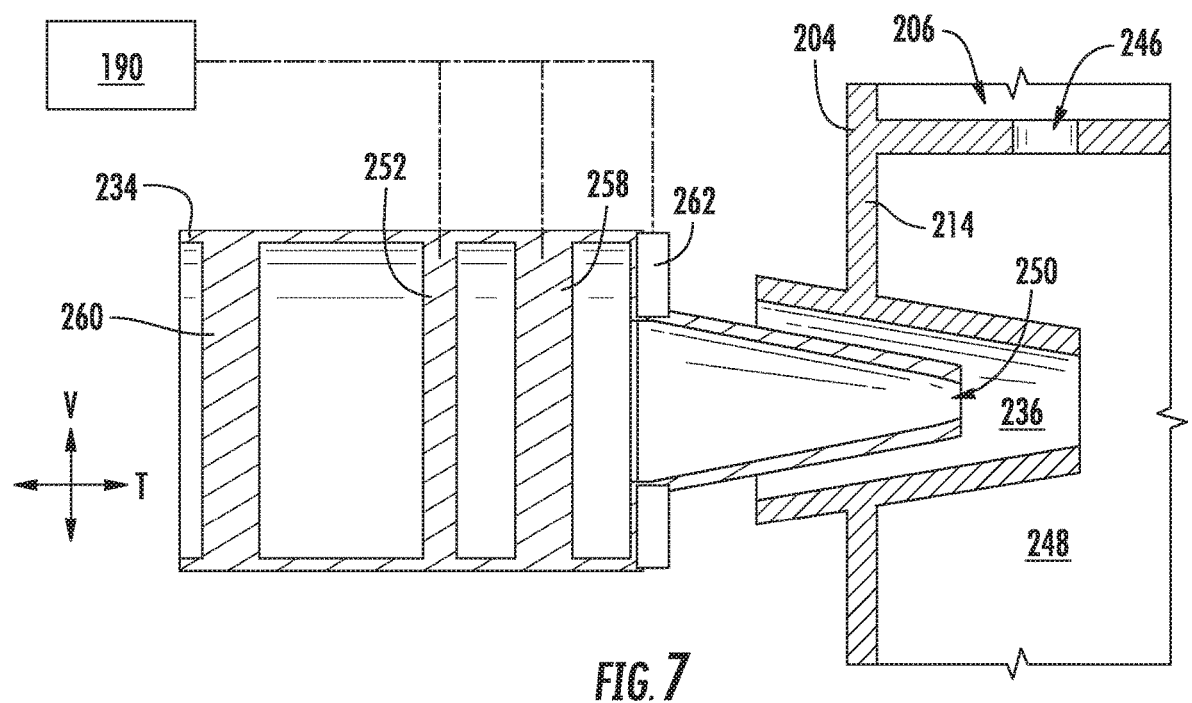
FIG. 7 provides a cross-sectional schematic view of a portion of the example storage assembly of FIG. 6 in an unengaged position.

Turning now to FIGS. 6 and 7, several cross-sectional schematic views of portions of storage assembly 200, including air conduit 234 and storage bin 204 are provided. Generally, FIG. 6 provides a view of storage assembly 200 in an engaged position, and FIG. 7 provides a view of storage assembly 200 in an unengaged position. As illustrated, an air handler 252 (e.g., fan or blower) is disposed in fluid communication with air conduit 234. Specifically, air handler 252 may be positioned within air conduit 234 to selectively direct or motivate gas, such as gaseous ozone through (e.g., to and/or from) ozone passage 236. In some embodiments, air handler 252 is a reversible fan. Optionally, air handler 252 may be operably coupled to controller 190. During certain operations, air handler 252 may direct gas (e.g., air and/or ozone) in a first flow direction (indicated by arrows 254) from air conduit 234 to ozone passage 236 and/or storage volume 206. During other operations, air handler 252 may direct gas (e.g., air and/or ozone) in a second flow direction (indicated by arrows 256) from storage volume 206 to air conduit 234.

In some embodiments, an ozone generator 258 is disposed in fluid communication with air conduit 234 to selectively supply gaseous ozone to storage volume 206 (e.g., through air conduit 234). In turn, when storage assembly 200 is in the engaged position, ozone generator 258 may be upstream of ozone passage 236 along the first flow direction 254 and downstream of ozone passage 236 along the second flow direction 256. Ozone generator 258 may be any suitable structure or assembly for producing selectively-producing gaseous ozone, such as a corona discharge ozone generator, ultraviolet light ozone generator, etc. When assembled, ozone generator 258 may be operably coupled to controller 190 and selectively activated to generate gaseous ozone (e.g., as directed by controller 190). Moreover, ozone generator 258 may be positioned within air conduit 234, as illustrated in FIGS. 6 and 7.

As shown, at least one conduit filter 260, such as an ozone filter, is disposed in fluid communication with air conduit 234. In certain embodiments, conduit filter 260 is positioned within air conduit 234 such that conduit filter 260 is upstream of air handler 252 along the first flow direction 254 and downstream of air handler 252 along the second flow direction 256. In further embodiments, conduit filter 260 is positioned within air conduit 234 such that conduit filter 260 is disposed upstream of ozone generator 258 along the first flow direction 254 and downstream of ozone generator 258 along the second flow direction 256. In turn, ozone generator 258 may be disposed between conduit filter 260 and ozone passage 236. Generally, conduit filter 260 may aid in ozone decomposition, e.g., to filter ozone passing from storage volume 206 through air conduit 234 in the second direction. Conduit filter 260 may be formed from any suitable semi-permeable material (e.g., a manganese oxide filter, activated carbon or charcoal, etc.) having one or more catalysts for facilitating or accelerating gaseous ozone decomposition.

A conduit sensor 262 is further provided in some embodiments to detect engagement between storage bin 204 and air conduit 234. Specifically, conduit sensor 262 may be configured to detect when storage bin 204 is in the engaged position and/or the unengaged position. In some such embodiments, conduit sensor 262 is operably coupled to controller 190. In turn, conduit sensor 262 may generally transmit signals (e.g., engagement signals) to and/or from controller 190 based on the position of storage bin 204.

When assembled, conduit sensor 262 is generally positioned or oriented to sense when storage bin 204 is moved to or from the engaged position. For instance, conduit sensor 262 may be provided on one or both of air conduit 234 and storage bin 204. Moreover, conduit sensor 262 may include a pressure sensor, proximity sensor, infrared sensor, contact sensor, or another suitable sensor, to detect that storage bin 204 has been positioned against air conduit 234 in the engaged position (e.g., when air conduit 234 is at least partially received within ozone passage 236).

Figure 8:
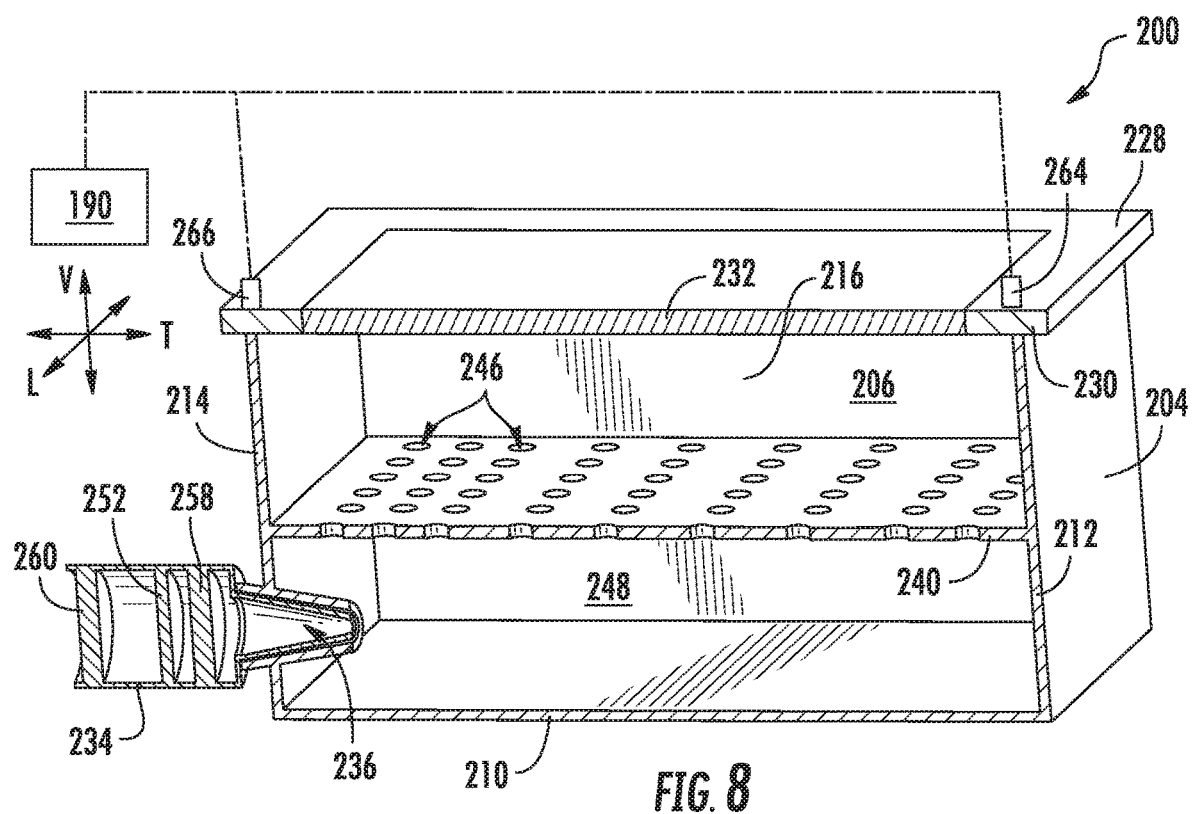
FIG. 8 provides a schematic view of a storage assembly of a refrigerator appliance according to example embodiments of the present disclosure.

Turning now to FIG. 8, a schematic view of a storage assembly 200 is shown. As generally indicated, some embodiments of storage assembly 200 include a cover lock 264, such as a complementary mechanical pair including a catch-latch, cavity-bolt, base-cam, etc. For instance, it is understood that one portion of cover lock 264 may be an active movable component (e.g., a latch, bolt, cam, etc.), while another portion may be a passive component (e.g., a catch, cavity, base, etc.). Cover lock 264 may be disposed between or across lid 228 and storage bin 204. In other words, the active component of cover lock 264 may be mounted or defined on lid 228 or storage bin 204 while the passive component is mounted or defined on the other of lid 228 or storage bin 204. The active component may thus be selectively moved to a position wherein the passive component is engaged and the cover lock 264 is fastened or locked. In turn, cover lock 264 may selectively hold lid 228 in a predetermined position relative to storage bin 204. In specific embodiments, cover lock 264 is configured to hold lid 228 against storage bin 204 or otherwise restrict lid 228 from moving from the closed position. Optionally, controller 190 may be operably coupled to cover lock 264 (e.g., at the active component). During operations, cover lock 264 may receive and/or transmit one or more lock signals to and/or from controller 190 (e.g., to move cover lock 264 to a position restricting movement of the lid 228).

In certain embodiments, a position sensor 266 is provided in operable communication (e.g., direct or indirect mechanical communication, electric communication, visual communication, etc.) with lid 228. Specifically, position sensor 266 may be configured to detect when lid 228 is in the closed position or open position. In some such embodiments, position sensor 266 is operably coupled to controller 190. In turn, position sensor 266 may generally transmit signals (e.g., engagement signals) to and/or from controller 190 based on the position of lid 228.

When assembled, position sensor 266 may be generally positioned or oriented to sense when lid 228 is moved to or from the closed position. For instance, position sensor 266 may be provided on one or both of lid 228 and storage bin 204. Moreover, position sensor 266 may include a pressure sensor, proximity sensor, infrared sensor, contact sensor, accelerometer, gyroscope, or another suitable sensor, to detect that lid 228 has been positioned against air storage bin 204 in the closed position. Although position sensor 266 is generally illustrated as a separate component from cover lock 264, alternative embodiments may provide position sensor 266 as part of cover lock 264.

As shown in FIG. 8, multiple ozone filters may be provided in some embodiments. For instance, conduit filter 260 (e.g., a first ozone filter) may be positioned in fluid communication with storage volume 206 (e.g., within air conduit 234). When assembled, conduit filter 260 may be disposed downstream of the storage volume 206 and/or ozone generator 258 (e.g., along the second flow direction). In turn, conduit filter 260 may facilitate or accelerate ozone decomposition as ozone is evacuated from storage volume 206 (e.g., to the ambient environment relative to refrigerator appliance 100—FIG. 2). Lid filter 232 (e.g., a second ozone filter) may further be positioned in fluid communication with storage volume 206. As an example, lid filter 232 may be positioned on lid body 230 above storage volume 206 (e.g., when lid 228 is in the closed position). When assembled, lid filter 232 may thus be disposed downstream of storage volume 206 and/or ozone generator 258 (e.g., along the first flow direction). In turn, lid filter 232 may facilitate or accelerate ozone decomposition as gaseous ozone is evacuated from storage volume 206 (e.g., to cavity 202 and/or fresh food chamber 122—FIGS. 2 and 3).

During certain operations, gaseous ozone may be generated by ozone generator 258 and provided to storage volume 206 in the first flow direction (e.g., as motivated by air handler 252). At least a portion of the gaseous ozone within storage volume 206 may flow to lid 228, where it may pass to lid filter 232 before escaping storage assembly 200 (e.g., as gaseous oxygen). During other operations, gaseous ozone may be evacuated from storage volume 206 through air conduit 234 in the second flow direction (e.g., as motivated by air handler 252). Gaseous ozone passing through ozone passage 236 may enter air conduit 234 before traveling to conduit filter 260. Gaseous ozone may decompose through conduit filter 260 before continuing through air conduit 234 and escaping storage assembly 200 (e.g., to the ambient environment).

Advantageously, gaseous ozone may be supplied to food items within storage bin 204 without unduly raising the concentration of ozone within the surrounding portions of the chilled chamber. A user may generally access, for instance, the fresh food chamber 122 freely without risking undesired ozone exposure.

Figure 9:
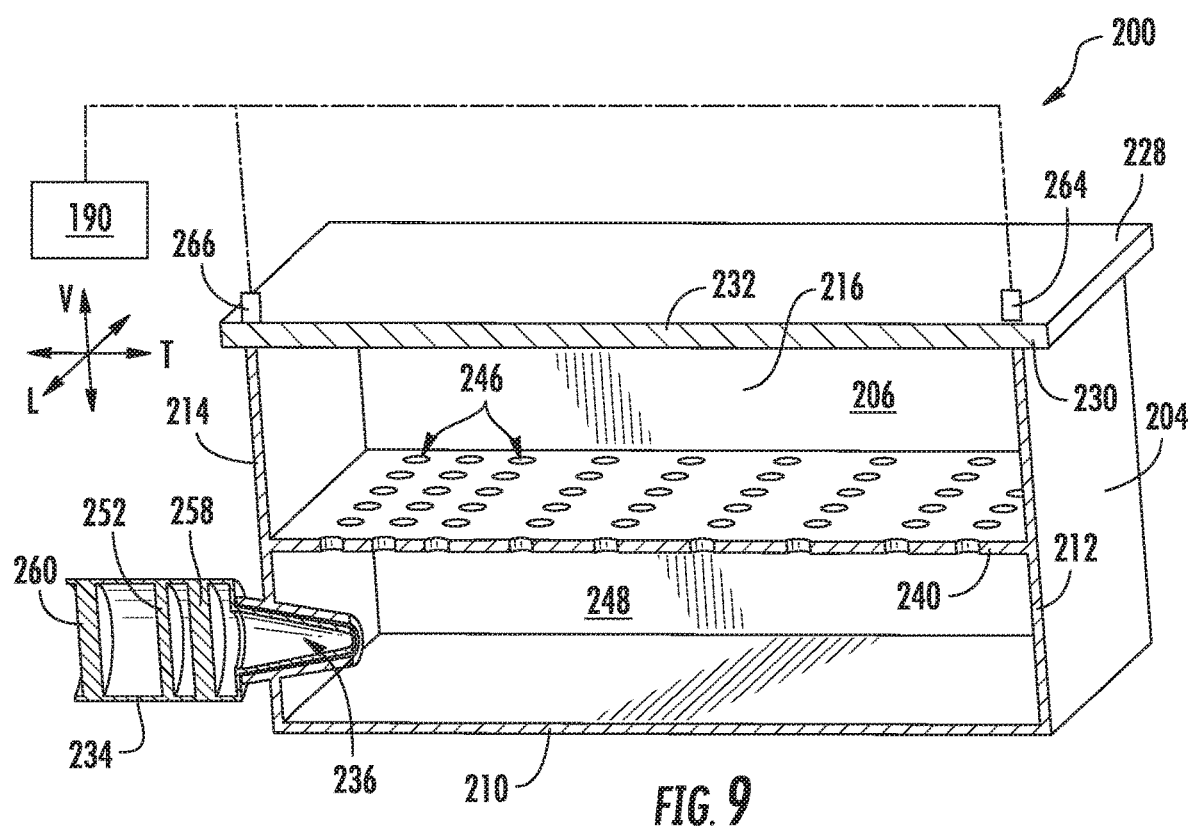
FIG. 9 provides a schematic view of a storage assembly of a refrigerator appliance according to other example embodiments of the present disclosure.
Figure 10:
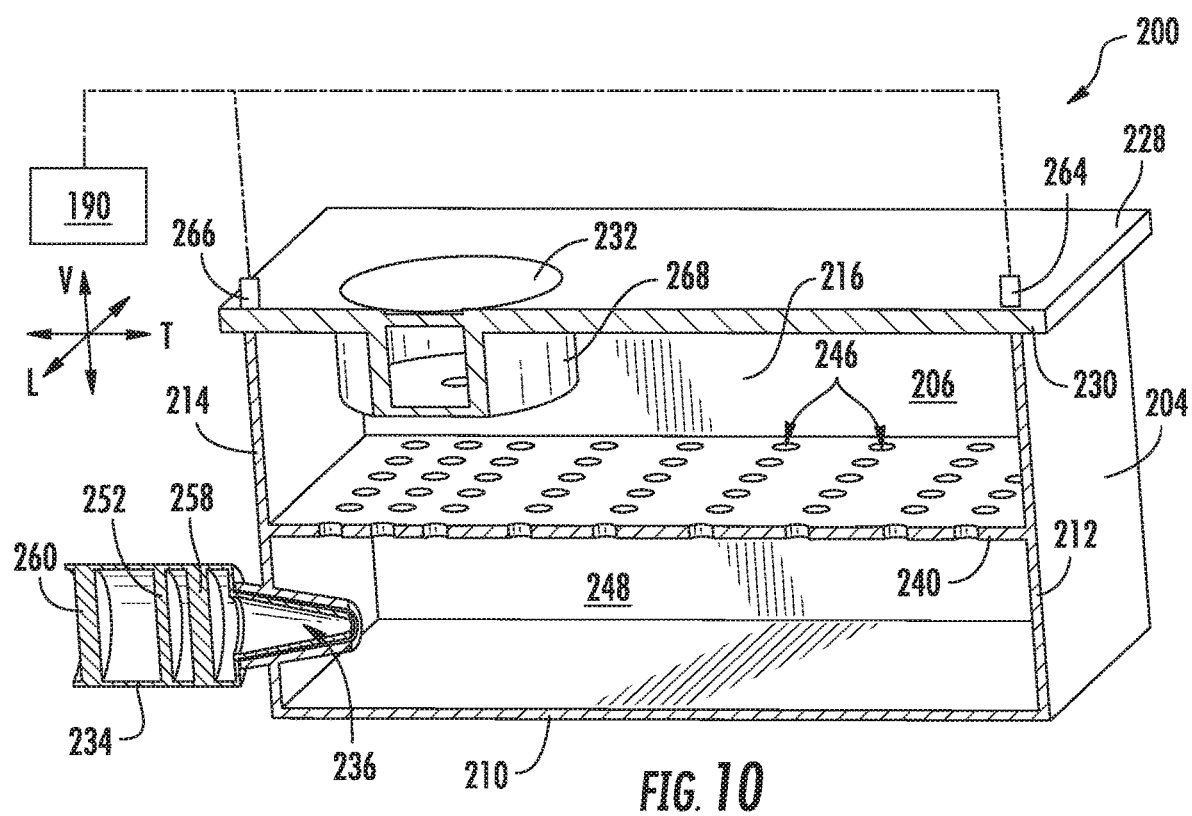
FIG. 10 provides a schematic view of a storage assembly of a refrigerator appliance according to more example embodiments of the present disclosure.
Figure 11:
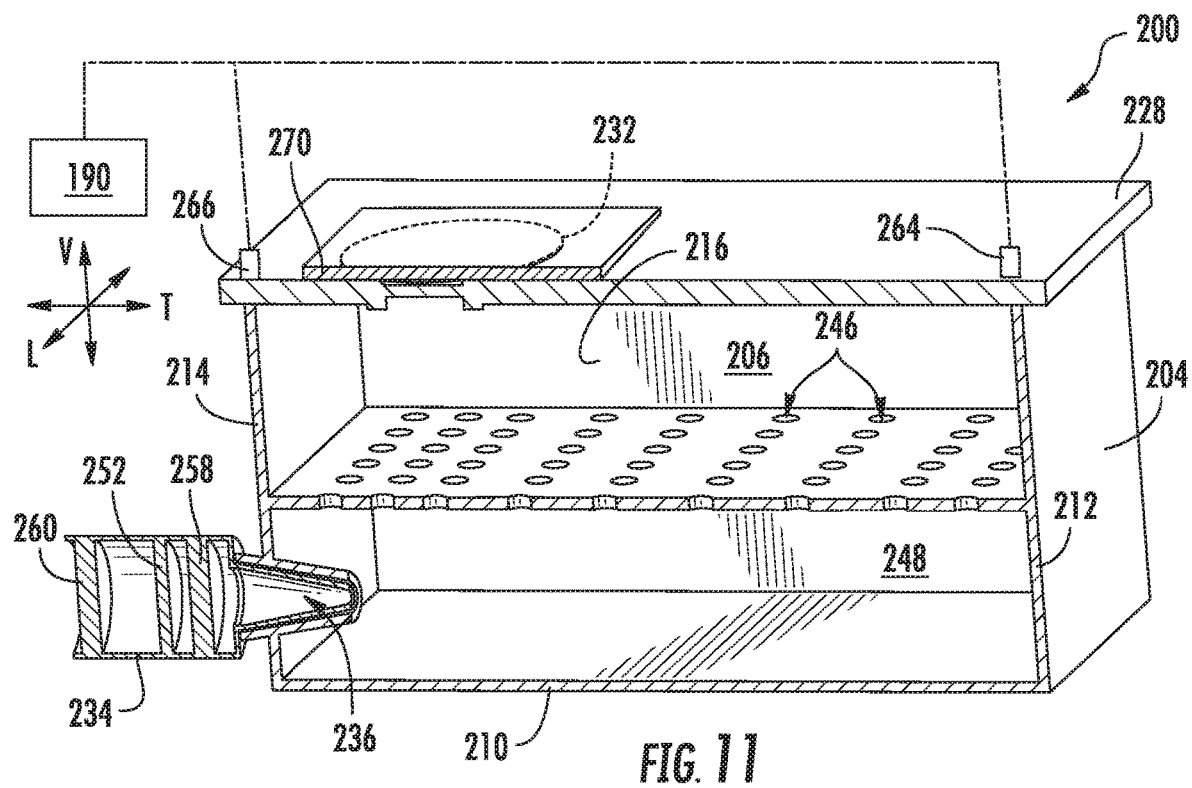
FIG. 11 provides a schematic view of a storage assembly of a refrigerator appliance according to still more example embodiments of the present disclosure.

Turning now to FIGS. 9 through 11, various alternative example embodiments of storage assembly 200 of refrigerator appliance 100 (FIGS. 1 and 2) are illustrated in corresponding schematic views. Except as otherwise indicated, it is understood that the embodiments of FIGS. 9 through 11 are substantially similar to the embodiments described above with respect to FIGS. 1 through 8. In turn, the same identifying numerals are generally used throughout. Moreover, it is also understood that the embodiments of FIGS. 9 through 11 could be modified to include features of the embodiments of FIGS. 1 through 8, and vice versa, except as otherwise indicated.

As shown in FIG. 9, some embodiments of storage assembly 200 include a solid lid 228. Lid body 230 may thus be provided as a solid, non-permeable member that is free of any apertures 246 through which air or ozone may pass therethrough. In some such embodiments, lid 228 forms a hermetic seal with storage bin 204 in the closed position. When assembled in the closed position, lid 228 may thus contain gas (e.g., gaseous ozone) within storage volume 206 and fluidly isolate storage volume 206 from fresh food chamber 122 (FIG. 2) and/or cavity 202 (FIG. 3).

During certain operations, gaseous ozone may be generated by ozone generator 258 and provided to storage volume 206 in a first flow direction (e.g., as motivated by air handler 252). The gaseous ozone within storage volume 206 may be sealed or held therein (e.g., beneath lid 228 and between walls 210, 212, 214, 216), such that virtually no ozone passes into the surrounding portions of the chilled chamber. During other operations, gaseous ozone may be evacuated from storage volume 206 through air conduit 234 in a second flow direction (e.g., as motivated by air handler 252). Gaseous ozone passing through ozone passage 236 may enter air conduit 234 before traveling to conduit filter 260. Gaseous ozone may decompose through conduit filter 260 before continuing through air conduit 234 and escaping storage assembly 200 (e.g., to the ambient environment).

As shown in FIG. 10, some embodiments of storage assembly 200 include a pressure relief valve 268. As an example, pressure relief valve 268 may be attached to lid body 230. Pressure relief valve 268 may further be disposed in fluid communication with an ozone filter (e.g., lid filter 232). In some such embodiments, lid filter 232 is included within a portion of lid 228, e.g., downstream from pressure relief valve 268 in a first flow direction. Pressure relief valve 268 may generally be configured to selectively open or permit gas therethrough at or above a predetermined pressure. When assembled in the closed position, pressure lid 228 valve remains closed below the predetermined pressure. Lid 228 may thus contain gas (e.g., gaseous ozone) within storage volume 206 below the predetermined pressure. Moreover, lid 228 may fluidly isolate storage volume 206 from a fresh food chamber 122 (FIG. 2) and/or cavity 202 (FIG. 3). By contrast, when the pressure within storage volume 206 exceeds the predetermined pressure, pressure relief valve 268 may open, releasing gas (e.g., gaseous ozone) through the pressure relief valve 268 and/or lid 228.

During certain operations, gaseous ozone may be generated by ozone generator 258 and provided to storage volume 206 in the first flow direction (e.g., as motivated by air handler 252). When, or as long as, the pressure within storage volume 206 remains below the predetermined pressure, the gaseous ozone within storage volume 206 may be sealed or held therein (e.g., beneath lid 228 and between walls 210, 212, 214, 216), such that virtually no ozone passes into the surrounding portions of the chilled chamber. Upon pressure within storage volume 206 meeting or exceeding the predetermined pressure, at least a portion of the gaseous ozone within storage volume 206 may flow through pressure relief valve 268 where it may pass to lid filter 232 before escaping storage assembly 200 (e.g., as gaseous oxygen). During other operations, gaseous ozone may be evacuated from storage volume 206 through air conduit 234 in a second flow direction (e.g., as motivated by air handler 252). Gaseous ozone passing through ozone passage 236 may enter air conduit 234 before traveling to conduit filter 260. Gaseous ozone may decompose through conduit filter 260 before continuing through air conduit 234 and escaping storage assembly 200 (e.g., to the ambient environment).

As shown in FIG. 11, some embodiments of storage assembly 200 include a movable solid damper 270. As an example, solid damper 270 may be movably attached to lid body 230 as a solid, non-permeable member. Solid damper 270 may further be disposed in fluid communication with an ozone filter (e.g., lid filter 232) to selectively cover the filter 232. In some such embodiments, lid filter 232 is included within a portion of lid 228, e.g., upstream from solid damper 270 in a first flow direction. Solid damper 270 may generally be configured to selectively move between a sealed and an unsealed position. In the unsealed position, solid damper 270 may be positioned away from lid filter 232, thereby permitting gas through lid filter 232 (e.g., in the first flow direction). In the sealed position, solid damper 270 may be positioned over or across lid filter 232, thereby restricting or preventing gas through lid filter 232 (e.g., in the first flow direction). When assembled in the closed position and the sealed position, lid 228 may thus contain gas (e.g., gaseous ozone) within storage volume 206 below the predetermined pressure. Moreover, lid 228 may fluidly isolate storage volume 206 from fresh food chamber 122 (FIG. 2) and/or cavity 202 (FIG. 3).

During certain operations, gaseous ozone may be generated by ozone generator 258 and provided to storage volume 206 in the first flow direction (e.g., as motivated by air handler 252). When, or as long as, the solid damper 270 is in the sealed position, the gaseous ozone within storage volume 206 may be sealed or held therein (e.g., beneath lid 228 and between walls 210, 212, 214, 216), such that virtually no ozone passes into the surrounding portions of the chilled chamber. When, or as long as, the solid damper 270 is in the unsealed position, at least a portion of the gaseous ozone within storage volume 206 may flow to lid filter 232 before escaping storage assembly 200 (e.g., as gaseous oxygen). During other operations, gaseous ozone may be evacuated from storage volume 206 through air conduit 234 in a second flow direction (e.g., as motivated by air handler 252). Gaseous ozone passing through ozone passage 236 may enter air conduit 234 before traveling to conduit filter 260. Gaseous ozone may decompose through conduit filter 260 before continuing through air conduit 234 and escaping storage assembly 200 (e.g., to the ambient environment).

Figure 12:
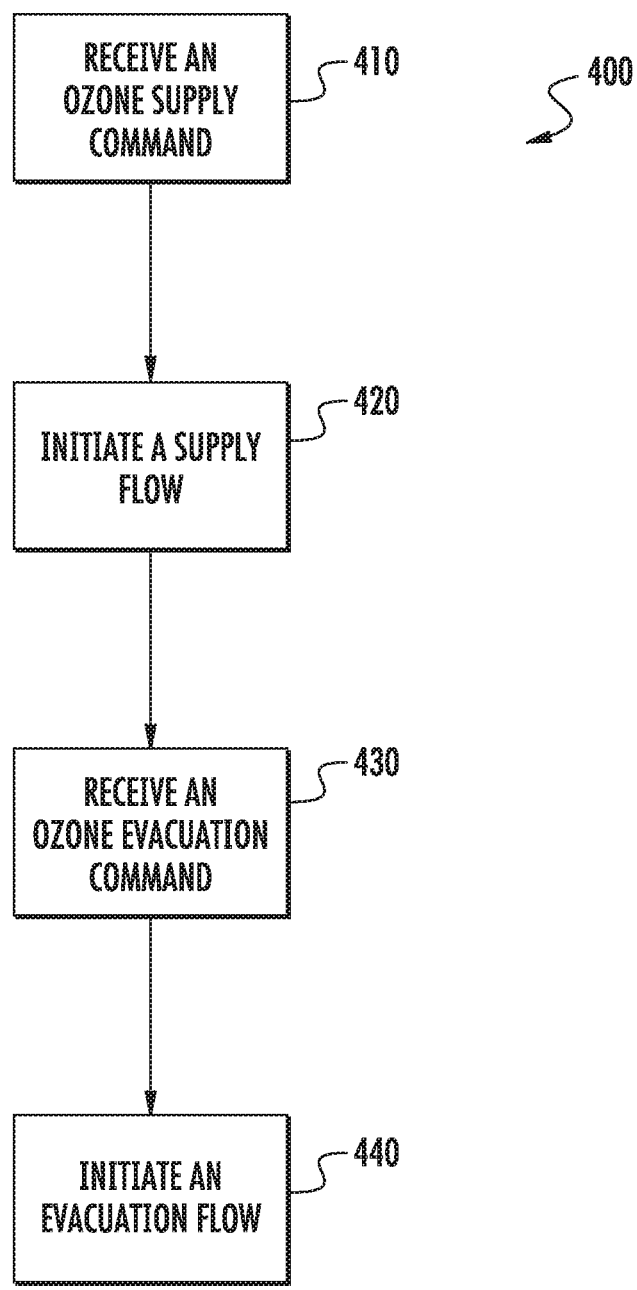
FIG. 12 provides a flow chart illustrating a method of operating a refrigerator appliance in accordance with example embodiments of the present disclosure.

Turning now to FIGS. 12 and 13, flow charts are provided of methods 400 and 500 according to example embodiments of the present disclosure. Generally, the methods 400 and 500 provide for methods of operating a refrigeration appliance 100 (FIG. 1) that includes a storage bin 204 and lid 228 (FIG. 3), as described above. The methods 400 and 500 can be performed, for instance, by the controller 190 (FIG. 1). For example, controller 190 may, as discussed, be operatively coupled to one or more sensors 262 and/or 266, ozone generator 258, air handler 252, cover lock 264, and user interface panel 148. During operations, controller 190 may send signals to and receive signals from sensors 262 and/or 266, ozone generator 258, air handler 252, cover lock 264, and user interface panel 148. Controller 190 may further be operatively coupled to other suitable components of the appliance 100 to facilitate operation of the appliance 100 generally. FIGS. 4 and 5 depict steps performed in a particular order for purpose of illustration and discussion. Those of ordinary skill in the art, using the disclosures provided herein, will understand that the steps of any of the methods disclosed herein can be modified, adapted, rearranged, omitted, or expanded in various ways without deviating from the scope of the present disclosure. For instance, it is understood that method 500 may be used in the context of method 400, or vice versa.

Referring to FIG. 12, at 410, the method 400 includes receiving a closed lid signal. For instance, the closed lid signal may be transmitted from the position sensor in operative communication with the lid. The closed lid signal may generally indicate that lid has been moved to and/or remains in the closed position, as described above.

At 420, the method 400 includes initiating a supply flow of ozone in a first flow direction. Specifically, ozone may be gaseous ozone flowed from the air conduit to the storage volume (e.g., through the ozone passage). In some such embodiments, the ozone generator is activated within air conduit to produce the gaseous ozone. Additionally or alternatively, the air handler may be activated within the air conduit to motivate or direct ozone therethrough in the first flow direction. For instance, the air handler may initiate a flow of air through the air conduit. The air may pass through the ozone generator, such that gaseous ozone is produced and entrained with the flow of air as gaseous ozone is supplied to the storage volume. In further embodiments, 420 includes directing the cover lock to an engaged or restricting position. In turn, the lid may be restricted from opening or otherwise moving from the closed position.

In optional embodiments, 420 is initiated in response to receiving an ozone supply command. For instance, the ozone supply command may be transmitted upon determining a preset daily time has been reached. Additionally or alternatively, the ozone supply command is transmitted in response to a user input signal. For instance, a signal may be transmitted upon a user input being supplied at the user interface. Optionally, at 420, the air handler may be activated for a set amount of time or until a desired level of ozone has been reached within the storage volume.

At 430, the method 400 includes receiving an ozone evacuation command. In some embodiments, 430 includes receiving a user input signal (e.g., from the user interface). Optionally, such a user input signal may generally indicate or be transmitted when a user wishes to access the storage volume.

At 440, the method 400 includes initiating an evacuation flow of ozone in a second flow direction. Specifically, ozone may be gaseous ozone flowed from the storage volume to the air conduit (e.g., through the ozone passage). For instance, the air handler may be activated within the air conduit to motivate or direct ozone therethrough in the second flow direction. If the air handler is a reversible fan, the direction of rotation may be reversed from the first flow direction. The ozone may pass through the conduit filter, such that gaseous ozone is decomposed as oxygen before continuing through air conduit (e.g., to the ambient environment). Optionally, at 440, the air handler may be activated for a set amount of time or until a desired level of ozone has been reached within the storage volume. In further embodiments, 440 include directing the cover lock to a released or unengaged position. In turn, the lid may be permitted to open or otherwise move from the closed position.

Referring to FIG. 13, at 510, the method 500 includes preparing a storage assembly for ozone. Specifically, 510 includes determining the storage bin is at a rearward engaged position. For instance, an engaged signal may be transmitted from the conduit sensor in response to the storage bin being moved to the engaged position. As shown, 510 further includes evaluating whether the lid is locked in the closed position. If the lid is not evaluated as being locked, the cover lock may be activated to hold the lid in the closed position before again determining the storage bin is in the rearward engaged position. If the lid is evaluated as being locked, an ozone cycle may be commenced.

At 520, the method 500 includes initiating an ozone supply flow in response to the commencement of the ozone cycle. For instance, gaseous ozone is from the air conduit to the storage volume (e.g., through the ozone passage). The ozone generator is activated within air conduit. Moreover, the air handler is activated within the air conduit to motivate or direct ozone therethrough in a first flow direction. The air may pass through the ozone generator, such that gaseous ozone is produced and entrained with the flow of air as gaseous ozone is supplied to the storage volume. At 520, the air handler may be activated for a set amount of time or until a desired level of ozone has been reached within the storage volume.

At 530, the method 500 includes initiating an ozone evacuation flow. Specifically, ozone may be gaseous ozone flowed from the storage volume to the air conduit (e.g., through the ozone passage). For instance, the air handler may be activated within the air conduit to motivate or direct ozone therethrough in a second flow direction. The ozone may pass through the conduit filter, such that gaseous ozone is decomposed as oxygen before continuing through air conduit (e.g., to the ambient environment). In some such embodiments, 530 is initiated in response to another condition (e.g., the elapse of a set amount of time subsequent to 520 or desired ozone level within storage volume).

At 540, the method 500 includes finalizing the ozone cycle. Specifically, 540 includes determining the ozone cycle is complete. For instance, it may be determined that the air handler has operated in a second flow direction for a predetermined amount of time. Additionally or alternatively, it may be determined that a desired ozone level (e.g., below 50 ppb) has been reached within the storage volume. Upon the determination of the ozone cycle being complete, 540 includes receiving a release signal and release the cover lock, permitting the lid to move away from the closed position. In turn, the storage volume may be accessed, e.g., by a user.

At 555, the method 500 includes receiving an unlock request, e.g., as user input signal. The unlock request may be received at any moment of the ozone cycle. For instance, a user may engage the user interface or another switch to indicate that access to the storage volume is desired.

At 565, the method 500 includes evaluating the suitability of the storage volume. Specifically, 565 includes evaluating the unlock request. If the request is not conditional (e.g., not predicated on an immediate condition being met), the method 500 may move immediately to 540. If the request is conditional (e.g., predicated on an immediate condition being met), 565 may include evaluating whether further ozone is required (e.g., for adequate food preservation). If further ozone is evaluated as being required, the method 500 may return to 520. If further ozone is evaluated as not being required, the method 500 may proceed to 575.

At 575, the method 500 includes determining the immediate condition has been met. For instance, the immediate condition may include requiring a set amount of time to elapse from receiving the unlock request at 565. Additionally or alternatively, the immediate condition may include a maximum ozone concentration within storage volume. In other words, the immediate condition may prescribe an ozone concentration below which the storage volume should be (e.g., less than 50 ppb). Also additionally or alternatively, the immediate condition may relate to the position of storage bin. For instance, the immediate condition may include storage bin being in the unengaged position.

At 585, the method 500 includes examining the state of the cycle. Specifically, 585 includes evaluating whether the ozone evacuation flow is in progress. If the supply flow is in progress (e.g., ozone is being supplied to the storage volume in a first flow direction), 585 includes transmitting an override signal and proceeding to 530. If no supply flow is in progress, method 500 may proceed to 540.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A refrigerator appliance comprising:
    a cabinet defining a chilled chamber;
    a storage bin positioned within the chilled chamber, the storage bin comprising a plurality of walls defining a storage volume;
    a lid positioned on the storage bin to selectively cover the storage volume in a closed position;
    an ozone passage defined through at least one of the plurality of walls in fluid communication with the storage volume;
    an air conduit disposed in selective fluid communication with the ozone passage;
    an air handler disposed in fluid communication with the air conduit to direct ozone through the ozone passage; and
    an ozone filter disposed in fluid communication with the air conduit to filter ozone passing from the storage volume through the air conduit,
    wherein the ozone filter is a first ozone filter, and wherein the lid comprises a lid body and a second ozone filter positioned on the lid body above the storage volume.

2. The refrigerator appliance of claim 1, further comprising an ozone generator disposed in fluid communication between the ozone filter and the ozone passage.

3. The refrigerator appliance of claim 1, further comprising a distributer plate positioned within the storage bin in fluid communication between the ozone passage and the storage volume.

4. The refrigerator appliance of claim 1, wherein the plurality of walls comprises a rear wall facing a rear portion of the chilled chamber, wherein the air conduit defines a port behind the storage bin at the rear portion of the chilled chamber, and wherein the ozone passage is defined through the rear wall to selectively engage the port.

5. The refrigerator appliance of claim 1, wherein the lid further comprises a pressure relief valve positioned on the lid body in fluid communication with the second ozone filter.

6. The refrigerator appliance of claim 1, wherein the air handler is a reversible fan configured to alternately direct air in a first flow direction from the air conduit to the storage volume and a second flow direction from the storage volume to the air conduit.

7. The refrigerator appliance of claim 6, further comprising a controller operably coupled to the air handler and configured to execute a clean air sequence comprising
receiving an ozone supply command,
initiating a supply flow in the first flow direction in response to receiving the ozone supply command,
receiving an ozone evacuation command, and
initiating an evacuation flow in the second flow direction in response to receiving the ozone evacuation command.

8. The refrigerator appliance of claim 7, further comprising a position sensor in operable communication with the lid in the closed position, and wherein receiving the ozone supply command comprises receiving a closed lid signal from the position sensor.

9. The refrigerator appliance of claim 7, wherein the clean air sequence further comprises determining a preset daily time has been reached, wherein the ozone supply command is received upon determining the preset daily time has been reached.

10. The refrigerator appliance of claim 7, further comprising a cover lock operably coupled to the controller in operable communication with the lid in the closed position, and wherein initiating a supply flow comprises directing the cover lock to a position restricting opening of the lid from the closed position.

11. The refrigerator appliance of claim 7, further comprising a user interface operably coupled to the controller, wherein receiving the ozone evacuation command comprises receiving a user input signal from the user interface.

12. The refrigerator appliance of claim 7, further comprising a user interface operably coupled to the controller, wherein receiving the ozone supply command comprises receiving a user input signal from the user interface.

13. A method of operating a refrigerator appliance comprising a cabinet defining a chilled chamber, a storage bin defining a storage volume, a lid positioned on the storage bin to selectively cover the storage volume in a closed position, an ozone passage defined through at least one of the plurality of walls in fluid communication with the storage volume, an air conduit disposed in selective fluid communication with the ozone passage, an air handler disposed in fluid communication with the air conduit to direct ozone through the ozone passage, a first ozone filter disposed in fluid communication with the air conduit to filter ozone passing from the storage volume through the air conduit, a second ozone filter positioned on the lid above the storage volume, the method comprising:
receiving a closed lid signal from a position sensor in operable communication with the lid;
initiating a supply flow of ozone in a first flow direction from the air conduit to the storage volume in response to receiving the closed lid signal;
receiving an ozone evacuation command; and
initiating an evacuation flow of ozone in a second flow direction from the storage volume to the air conduit in response to receiving the ozone evacuation command.

14. The method of claim 13, further comprising receiving an ozone supply command upon determining a preset daily time has been reached, wherein initiating the supply flow is further in response to receiving the ozone supply command.

15. The method of claim 13, wherein initiating the supply flow of ozone comprises directing a cover lock to a position restricting opening of the lid from the closed position.

16. The method of claim 13, wherein receiving the ozone evacuation command comprises receiving a user input signal from a user interface.

17. The method of claim 13, further comprising receiving an ozone supply command, wherein initiating the supply flow is further in response to receiving the ozone supply command, and wherein receiving the ozone supply command comprises receiving a user input signal from a user interface.

* * * * *